(12) United States Patent
Franklin

(10) Patent No.: US 6,251,377 B1
(45) Date of Patent: *Jun. 26, 2001

(54) COSMETIC COMPOSITIONS

(75) Inventor: Kevin Ronald Franklin, Wirral (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/592,130

(22) Filed: Jun. 12, 2000

(30) Foreign Application Priority Data

Jun. 15, 1999 (GB) .................................. 9913954

(51) Int. Cl.⁷ .............................. A61K 7/32; A61K 7/34; A61K 7/38; A61K 7/00
(52) U.S. Cl. ................ 424/65; 424/66; 424/68; 424/400; 424/401
(58) Field of Search .................... 424/65, 66, 68, 424/400, 401

(56) References Cited

U.S. PATENT DOCUMENTS 4,894,222  1/1990  Matravers .

FOREIGN PATENT DOCUMENTS

090/188604  7/1997  (JP) .
97/11678    4/1997  (WO) .

OTHER PUBLICATIONS

Search Report under Section 17(5) Application No. GB 9913954.5 dated Oct. 21, 1999.

*Primary Examiner*—Shelley A. Dodson
(74) *Attorney, Agent, or Firm*—Matthew Boxer

(57) ABSTRACT

A cosmetic composition, preferably an antiperspirant stick, has a carrier liquid which is almost exclusively silicone oil, structured with lanosterol. Instability is avoided by nearly complete exclusion or complete exclusion of silicon-free organic liquids.

21 Claims, No Drawings

COSMETIC COMPOSITIONS

The following U.S. patent applicaton are co-pending with, and commonly assigned with, the present application:

U.S. Ser. No. 09/548,309 to Franklin et al., filed Apr. 12, 2000;

U.S. Ser. No. 09/548,310 to Franklin et al., filed Apr. 12, 2000;

U.S. Ser. No. 09/547,804 to Franklin et al., filed Apr. 11, 2000;

U.S. Ser. No. 09/547,604 to Franklin et al., filed Apr. 12, 2000;

U.S. Ser. No. 09/547,445 to Esser et al., filed Apr. 12, 2000; and

U.S. Ser. No. 09/547,625 to Franklin et al., filed Apr. 12, 2000."

FIELD OF THE INVENTION

The present invention relates to cosmetic compositions for application to human skin. Significant forms of the invention are concerned with antiperspirant compositions for application to human skin, especially the axilla. However, the invention can also be applied to other forms of cosmetic composition.

BACKGROUND OF THE INVENTION AND SUMMARY OF PRIOR ART

A wide variety of cosmetic compositions for application to human skin make use of a structured liquid carrier to deliver colour or some other active material to the surface of the skin. A significant example of such cosmetic compositions are antiperspirant compositions which are widely used in order to enable their users to avoid or minimise wet patches on their skin, especially in axillary regions.

Antiperspirant formulations have been provided with a range of different product forms. One of these is a so-called "stick" which is usually a bar of an apparently firm solid material held within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact.

Antiperspirant sticks can be divided into three categories. Suspension sticks contain a particulate antiperspirant active material suspended in a structured carrier liquid phase. Emulsion sticks normally have a hydrophilic phase containing the antiperspirant active in solution, this phase forming an emulsion with a second, more hydrophobic, liquid phase. The continuous phase of the emulsion is structured. Solution sticks typically have the antiperspirant active dissolved in a structured liquid phase which may be a mixture of water and a water-miscible organic solvent.

Other types of cosmetic composition can also be provided in the form of a stick and again the stick may be a structured solution, emulsion or suspension. Examples of cosmetic compositions which are, or can be, marketed in a stick form are lipsticks, lip salves and eyebrow pencils.

There is substantial literature on the structuring of cosmetic compositions.

Conventionally, many sticks have been structured using naturally-occurring or synthetic waxy materials. Examples of these include those fatty alcohols which are solid at room temperature, such as stearyl alcohol, and hydrocarbon waxes or silicone waxes. Such materials are widely available, and by suitable selection of the materials themselves and their concentrations in the formulation, it is possible to obtain either a soft solid or a firm solid. Examples of wax-structured sticks are described in an article in Cosmetics and Toiletries, 1990, Vol 105, P75–78 and in U.S. Pat. Nos. 5,169,626 and 4,725,432. However, fatty alcohol or wax structured sticks tend to leave visible white deposits on application to human skin, and the deposits can also transfer onto clothing when it comes into contact with the skin and the wearer can, for example, find white marks at the armhole of the sleeveless garment.

Some alternative structurants have been proposed. The term "gellant" is often employed instead of "structurant". For example, the use of dibenzylidene sorbitol (DBS) or derivatives thereof as gellant has been proposed in a number of publications such as EP-A-512770, WO 92/19222, U.S. Pat. No. 4,954,333, U.S. Pat. No. 4,822,602 and U.S. Pat. No. 4,725,430.

In WO 97/11678 to Helene Curtis, Inc, there is described the use of lanosterol as a gellant to make soft gels, sometimes in conjunction with a starch hydrolyzate derivative for antiperspirant compositions. All the formulation examples contain both a volatile silicone oil and an organic solvent which is a silicon-free compound or mixture of compounds.

In WO 98/34588 to Lancaster Group GmbH, there is described the use of lanosterol as a gellant for oil-based cosmetic compositions, containing a cosmetic active material, of which one listed material is a deodorant, though not exemplified. The exemplified compositions contain hydrocarbon oils.

SUMMARY OF THE INVENTION

We have observed that if stick products are made using lanosterol as gellant for an oil phase which is a mixture of silicone oil and silicon-free organic solvent, the resulting sticks do not remain stable during storage. Crystals of lanosterol grow and form crystalline lumps in the stick which mar its appearance and give a gritty feel. The process can lead to loss of strength of the stick and leakage of solvent.

Surprisingly we have found that much better storage stability can be achieved if the oil phase is substantially free of any silicon-free organic compound which is liquid at 20° C.

According to a first aspect of the present invention there is provided a composition of matter suitable for cosmetic use having a continuous phase which comprises water-immiscible liquid carrier and a structurant therein wherein the structurant comprises lanosterol and the water-immiscible liquid carrier comprises one or more silicone oils, with not more than 3% (by weight of the liquid) of any silicon-free organic compounds which are liquid at 20° C. dissolved therein.

Preferably the content of any such silicon-free liquid organic compounds is not more than 2%, preferably not more than 1% (by weight of the liquid) and more preferably they are absent, so that the carrier liquid consists solely of silicone oil.

The lanosterol serves as a structuring agent for the liquid carrier which consists very largely or exclusively of silicone oil.

When used in a sufficient amount, which is likely to be less than 15% of the total composition, it is able to structure this liquid into a gel with sufficient rigidity to sustain its own shape.

Lanosterol may be the only structurant present. If any other structurant is used jointly with lanosterol the amount of it is likely to be less than the amount (by weight) of lanosterol. The amount of structurant is likely to be not over 15% of the formulation, better not over 10% or 12%.

Without being bound to any specific theory or explanation, it is believed that the lanosterol forms a network of interconnected strands extending throughout the carrier liquid phase. Upon heating the gel to a temperature referred to as the gel melting temperature, the strands of structurant dissolve and the liquid becomes more mobile.

The structurant water-immiscible carrier liquid may be the continuous phase of a composition with a dispersed solid phase suspended therein. It is especially envisaged that the composition will be an antiperspirant and the dispersed solid will be a particulate antiperspirant active.

Another, less preferred, possibility is that the carrier liquid is the continuous phase of an emulsion. Then the dispersed liquid phase may be a solution of antiperspirant active in water or other hydrophilic solvent.

A composition of this invention will generally be marketed in a container by means of which it can be applied at time of use. This container may be of conventional type.

A second aspect of the invention therefore provides a cosmetic product comprising a dispensing container having an aperture for delivery of the contents of the container, means for urging the contents of the container to the said aperture, and a composition of the first aspect of the invention in the container. Suitably, the aperture is an open end.

The compositions of this invention can be produced by conventional processes for making suspension, or as the case may be, emulsion solids.

Thus, according to a third aspect of the present invention there is provided a process for the production of a cosmetic composition comprising, not necessarily in any order, the steps of incorporating lanosterol as structurant into a water-immiscible liquid carrier which comprises one or more silicone oils with not more than 3% (by weight of the liquid) of any silicon-free organic compounds which are liquid at 20° C. dissolved therein, if required, mixing the liquid carrier with a solid or a disperse liquid phase to be suspended therein, heating the liquid carrier or a mixture containing it to an elevated temperature at which the structurant is soluble in the water-immiscible liquid carrier, followed by introducing the mixture into a mould which preferably is a dispensing container, and then cooling or permitting cooling of the mixture to a temperature at which it is solidified.

A suspended solid may be an antiperspirant active and a disperse phase may be a solution of such an active in a hydrophilic or polar solvent.

According to a fourth aspect of the present invention, there is provided a method for preventing or reducing perspiration on human skin comprising topically applying to the skin a composition comprising an antiperspirant active, a water-immiscible liquid carrier which comprises one or more silicone oils with not more than 3% (by weight of the liquid) of any silicon-free organic compounds which are liquid at 20° C. dissolved therein and lanosterol as a structurant therein.

DETAILED DESCRIPTION AND EMBODIMENTS

The various materials useful in this invention will now be discussed by turn and preferred features and possibilities will be indicated.

Lanosterol has the following chemical formula:

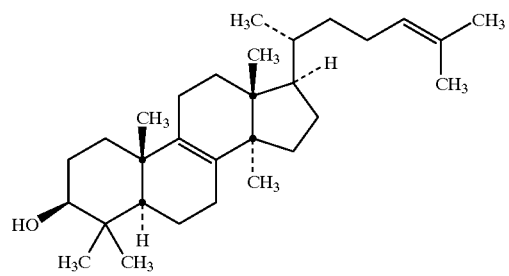

It is commercially available, and as supplied it contains some dihydrolanosterol. This impurity in the commercial material does not need to be removed.

The amount of lanosterol, including any dihydrolanosterol impurity, preferably lies in a range from 1 or 2% up to 10%, 12 or even 15% of the carrier liquid. The amount may be from 1% or 2% up to 8% of the whole composition especially when the composition takes the form of an antiperspirant stick. Possibly, the total amount of all structurants is not over 8% of the whole composition.

Carrier Liquid

The water-immiscible carrier liquid comprises a silicone oil or a mixture of silicone oils. These are relatively hydrophobic and are immiscible in water.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier must contain from 97% better 99% up to 100% by weight of one or more liquid silicones. Volatile silicone preferably constitutes from 20 to 100% of the weight of the carrier liquid. In many instances, when a non-volatile silicone oil is present, its weight ratio to volatile silicone oil is chosen in the range of from 1:3 to 1:40.

Liquid Disperse Phase

If the composition is an emulsion with the lanosterol serving as a structurant in the continuous phase, the emulsion will contain a more polar disperse phase. The disperse phase may be a solution of an active ingredient.

The hydrophilic disperse phase in an emulsion normally comprises water as solvent and can comprise one or more water-soluble or water-miscible liquids in addition to or replacement for water. The proportion of water in an emulsion according to the present invention is often selected in the range of up to 60%, and particularly from 10% up to 40% or 50% of the whole formulation.

One class of water-soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water-miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

Ethanol gives a cooling effect on application to skin, because it is very volatile. It is preferred that the content of ethanol or any monohydric alcohol with a vapour pressure above 1.3 kPa (10 mmHg) is not over 15% better no over 8% by weight of the composition.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with high proportion of disperse phase, i.e. from 65 to 85% disperse phase, may also be advantageous. They can give good hardness even though the concentration of structurant may be only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. $C_{16}$ to $C_{18}$ alcohols ethoxylated with 10 to 25 ethylene oxide residues) and PEG-15-25 stearate or distearate. Other suitable examples include $C_{10}$–$C_{20}$ fatty acid mono, di or triglycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPH™, Span™, Tween™, SF1228, DC3225C and Q2-5200.

An alternative to an emulsion, which is likely to be preferred for the sake of easier processing, is suspension with solid particles of an active ingredient suspended in the structured carrier liquid.

Antiperspirant Actives

If the composition is an antiperspirant, it will contain an antiperspirant active. Antiperspirant actives, are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the aqueous disperse phase, particularly from 10% or 20% up to 55% or 60% of that phase.

Alternatively, and preferably, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 $\mu$m with a mean particle size often from 3 to 20 $\mu$m. Both larger and smaller mean particle sizes can also be contemplated such as from 20 to 50 $\mu$m or 0.1 to 1 $\mu$m.

Optional Ingredients

Optional ingredients in compositions of this invention can include disinfectants, for example at a concentration of up to about 5% w/w provided they are not liquid. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™, Triclosan™, Tricloban™, and Chlorhexidine warrant specific mention. A yet another class comprises biguanide salts such as available under the trade mark Cosmosil™.

A further optional constituent of the formulation comprises one or more secondary structurants which can be employed in addition to the lanosterol which is the primary structurant. The amount of such secondary structurants in the formulation is often zero, and usually not more than 15% of the formulation. It is normally not greater than the amount of the primary structurant.

The secondary structurants employable herein can be non-polymeric or polymeric. Solid linear fatty alcohol and/or a wax may be included. It is preferred that a composition of this invention does not contain more than 5% by weight of any fatty alcohol which is solid at 20° C. Non-polymeric structurants, sometimes referred to as gellants, can be selected from fatty acids or salts thereof, such as stearic acid or sodium stearate or 12-hydroxy stearic acid. Other suitable gellants can comprise dibenzylidene alditols, e.g. dibenzylidene sorbitol. Further suitable gellants can comprise selected N-acyl amino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N' dialkylsuccinamides, e.g. dodecyl N,N'-dibutylsuccinamide.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly(phenyl substituted)siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, polyacrylamides, polyacrylates or polyalkylene oxides may be used to structure or thicken this aqueous phase.

The compositions herein can incorporate one or more cosmetic adjuncts which are conventional possibilities to include in antiperspirant or other cosmetic sticks. Such cosmetic adjuncts can include skin feel improvers, such as talc or finely divided polyethylene, for example in an amount of up to about 10%. A commonly employed adjunct is a perfume, which is normally present at a concentration of from 0 to 3% and in many formulations from 0.25 to 1.5% by weight of the composition.

Mechanical Properties and Product Packages

The compositions of this invention are structured liquids and it is an advantage that they may be firm in appearance.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

Generally the container will include a cap for its open end and a component part which is sometimes referred to as an "elevator" or "piston" fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions. (As will be mentioned below, this was followed by a measurement of the mean level of white deposits using image analysis).

The substrates used were a: 12×28 cm strip of grey abrasive paper (3M™ P800 WetnDry™ Carborundum paper)

b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed.

iii) Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

Preparation

Compositions of this invention can be produced by conventional processes for making suspension or emulsion solids. Such processes involve forming a heated mixture of the composition at a temperature which is sufficiently elevated that all the lanosterol structurant dissolves, pouring that mixture into a mould, which may take the form of a dispensing container, and then cooling the mixture whereupon the structurant solidifies into a network of interconnected fibres extending through the water-immiscible liquid phase.

A convenient process sequence for a composition which is a suspension comprises first forming a solution of the lanosterol structurant in the water-immiscible liquid. This is normally carried out by agitating the mixture at a temperature sufficiently high that all the structurant dissolves (the dissolution temperature) such as a temperature in a range from 50 to 120° C. Thereafter the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

In a suitable procedure for making emulsion formulations, a solution of the structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary; antiperspirant actives can sometime be supplied in aqueous solution which can be utilised as is). If possible, this solution of antiperspirant active which will become the disperse phase is heated to a temperature similar to that of the continuous phase with structurant therein, but without exceeding the boiling point of the solution, and then mixed with the continuous phase. Alternatively, the solution is introduced at a rate which maintains the temperature of the mixture. It may be necessary to work at a temperature above the boiling temperature of the disperse phase or a temperature at which evaporation of this phase is significant. If so, a pressurised apparatus could be used to allow a higher temperature to be reached. After two phases are mixed, the resulting mixture is filled into dispensing containers, typically at a temperature 5 to 30° C. above the setting temperature of the composition, and allowed to cool as described above for suspension sticks.

EXAMPLES

The examples below were prepared using a number of materials set out with their proprietary names in the following list. All temperature are in degrees Celsius.
1) Lanosterol (incorporating some dihydrolanosterol; from Croda Chemicals Ltd)
2) Volatile cyclic silicone fluid (cyclomethicone) DC 345 (Dow Corning)
3) Non-volatile silicone fluid DC 556 (Dow Corning)
4) Polydecene (Silkflo 364NF from Albemarle)
5) Isostearyl Alcohol (abbreviated to ISA—Prisorine 3515 from Unichema)
6) C12–15 alkyl benzoate (Finsolv TN from Fintex)
7) Isopropyl myristate (abbreviated to IPM; from Unichema)
8) Al/Zr Tetrachlorohydrex glycine complex (AZAG—7167 from Summit)
9) Al/Zr Tetrachlorohydrex glycine complex AZAG 6313-15 from Summit Examples 1–6 and Comparative Examples 7–10

Antiperspirant suspension sticks were prepared using a mixture of water-immiscible liquids, an antiperspirant active and lanosterol. In all cases the procedure was as follows:
the lanosterol and mixture of liquids was heated to a temperature at which the lanosterol had been observed to dissolve in a preliminary test. The resulting mixture was then allowed to cool whilst mixing gently until it reached a temperature of 10° above its gelling point. The particulate antiperspirant active was added to this solution and stirred in while maintaining the temperature. At this stage the mixture was poured into antiperspirant stick barrels and left to cool without further disturbance until the formulation had solidified.

The resulting sticks were evaluated after at least 24 hours at ambient laboratory temperature. In all cases the appearance of the stick was noted, and the hardness was determined by penetrometer. For Examples 5 and 6 tests of deposition and whiteness of the resulting deposit were carried out using the procedures described earlier. The sticks of these two examples were stored for one month at 50° C. and their hardness was determined again.

The formulations which were prepared and the properties of the resulting sticks are set out in the tablet below. The testing of hardness and whiteness of deposit was also carried out with a commercial white solid stick (CWS) structured with 15% stearyl alcohol and 3% castor wax, these percentages being by weight of its whole composition.

Examples 1–6 when newly made were all hard white opaque sticks. No visual change was observed with any of the sticks after 3 months at room temperature. Examples 5 and 6 showed no visible changes after 1 month storage at 50° C. (Examples 1 to 4 were not stored at 50° C.).

| Example | CWS | 1 | 2 | 3 | 4 | 5 | 6 |
|---|---|---|---|---|---|---|---|
| | | % by Weight | | | | | |
| Lanosterol | | 5 | 5 | 5 | 5 | 7 | 7 |
| Cyclomethicone, DC 345 | 73 | 70 | 61 | 60 | 58 | 58 | |
| DC 556 | | | 2 | 5 | 15 | 15 | 15 | 15 |
| AZAG 7167 | | 20 | 20 | 20 | 20 | 20 | |
| AZAG 6313-15 | | | | | | | 20 |
| | measurements of properties | | | | | | |
| penetration depth (mm) after 24 hours at ambient temperature | 9.4 | 9.1 | 9.2 | 11.2 | 9.8 | 7.3 | 8.1 |
| penetration depth (mm) after 1 month at 50° C. | | | | | | 7.1 | 8.2 |
| Whiteness on grey paper 24 hours after deposition | 118 | | | | | 25 | 26 |
| Whiteness on black wool 24 hours after deposition | 186 | | | | | 29 | 28 |

| Comparative Example | 7 | 8 | 9 | 10 |
|---|---|---|---|---|
| | % by Weight | | | |
| Lanosterol | 7 | 7 | 7 | 5 |
| Cyclomethicone, DC 345 | 58 | 56 | 68 | 70 |
| DC 556 | | 13 | | |
| Polydecene | 15 | — | — | — |
| Finsolv TN | — | — | 5 | — |
| Isostearyl alcohol | — | 4 | — | — |
| Isopropyl myristate | — | — | — | 5 |
| AZAG 7167 | — | — | — | 20 |
| AZAG 6313-15 | 20 | 20 | 20 | — |
| | measurement of properties | | | |
| penetration depth (mm) after 24 hours at ambient temperature | 10.5 | 10.8 | 12.3 | 13.2 |
| penetration depth (mm) after 1 month at 50° C. | too soft to measure | | | Very soft |
| Whiteness on grey paper 24 hours after deposition | 27 | | | |
| Whiteness on black wool 24 hours after deposition | 32 | | | |

Comparative Examples 7 to 10 when newly made were all hard slightly off-white opaque sticks. With all four of these comparative formulations a layer of fine crystals formed on the stick surface within 3 months at room temperature. These sticks felt rough and gritty when applied to skin.

After about 1 week at 50° C. comparative Examples 7, 8 and 9 began to leak solvent and large crystalline patches could be seen at the top and side surfaces of the sticks. After one month these three sticks had disintegrated into a slush.

What is claimed is:

1. A composition of matter suitable for cosmetic use having a continuous phase which comprises water-immiscible liquid carrier and a structurant therein wherein the structurant comprises lanosterol and the water-immiscible liquid carrier comprises from 97% to 100% (by weight of the liquid) of at least one silicone oil and from 0% to at most 3% (by weight of the liquid) of silicon-free organic compounds which are liquid at 20° C. dissolved in said silicone oil.

2. A composition according to claim 1 wherein the liquid carrier contains from 0% to at most 1% by weight of said silicon-free organic compounds which are liquid at 20° C.

3. A composition according to claim 1 wherein the liquid carrier consists exclusively of silicone oil and does not contain any silicon-free organic compounds which are liquid at 20° C.

4. A composition according to claim 1 wherein the water-immiscible liquid carrier contains a volatile silicone in an amount from 20 to 100% by weight of the liquid.

5. A composition according to claim 4 wherein the water-immiscible carrier liquid also contains non-volatile silicone oil, and the ratio of non-volatile to volatile silicone oils is in a range from 1:3 to 1:40.

6. A composition according to claim 1 containing from 0.1 to 15% by weight of the lanosterol structurant.

7. A composition according to claim 1 which contains from 0 to at most 5% by weight of any fatty alcohol which is solid at 20° C.

8. A composition according to claim 1 wherein the composition is an emulsion with a hydrophilic, preferably water-miscible, disperse phase in addition to a continuous phase of said water-immiscible liquid.

9. A composition according to claim 8 wherein the disperse phase contains a diol or polyol.

10. A composition according to claim 8 which contains from 0.1% to 10% by weight of a nonionic emulsifier.

11. A composition according to claim 1 wherein the composition is a suspension which a particulate solid material dispersed in said liquid continuous phase.

12. A composition according to claim 1 which is an antiperspirant composition comprising an antiperspirant active.

13. A composition according to claim 11 which is an antiperspirant composition comprising a particulate antiperspirant active in suspension in a continuous phase of said water-immiscible liquid.

14. A composition according to claim 8 which is an antiperspirant composition comprising an antiperspirant active dissolved in said disperse phase.

15. A composition according to claim 12 wherein the antiperspirant active comprises an aluminium and/or zirconium halohydrate, an activated aluminium and/or zirconium halohydrate, or an aluminium and/or zirconium complex or an activated aluminium and/or zirconium complex.

16. A composition according to claim 15 which is a halohydrate or complex in which aluminium and zirconium are both present.

17. A composition according to claim 12 wherein the proportion of antiperspirant active is from 5 to 40% by weight of the composition.

18. An antiperspirant product comprising a dispensing container having an open end for delivery of the contents of the container, means for urging the contents of the container to the said open end and a composition according to claim 12 accommodated within the container.

19. A process for the production of a cosmetic composition according to claim 1 comprising, in any order, the steps of incorporating lanosterol into a water-immiscible liquid carrier which comprises from 97 to 100% (by weight of the liquid) of at least one silicone oil and from 0% to at most 3% (by weight of the carrier liquid) of organic compounds which are silicon-free and liquid at 20° C. dissolved therein if required, mixing the liquid carrier with a solid or a disperse liquid phase to be suspended therein, heating the liquid carrier or a mixture containing it to an elevated temperature at which the structurant is soluble in the water-immiscible liquid carrier, followed by cooling or permitting cooling of the mixture to a temperature at which it is solidified.

20. A process according to claim 19 which includes a step of pouring the mixture at elevated temperature into a dispensing container and allowing it to cool therein so as to produce a product according to claim 18.

21. A method for preventing or reducing perspiration on human skin comprising topically applying to the skin a composition according to claim 12.

* * * * *